United States Patent [19]

Takahashi et al.

[11] Patent Number: 5,256,618
[45] Date of Patent: Oct. 26, 1993

[54] THERMOSENSITIVE RECORDING MATERIAL

[75] Inventors: Yoshiyuki Takahashi, Kawasaki; Akiko Iwasaki, Urawa; Kunitaka Toyofuku, Sakura, all of Japan

[73] Assignee: Oji Paper Co., Ltd., Tokyo, Japan

[21] Appl. No.: 955,193

[22] Filed: Oct. 2, 1992

[30] Foreign Application Priority Data

Oct. 4, 1991 [JP] Japan .................................. 3-257864
Apr. 30, 1992 [JP] Japan .................................. 4-111286
May 1, 1992 [JP] Japan .................................. 4-112838

[51] Int. Cl.$^5$ ............................................... B41M 5/30
[52] U.S. Cl. ...................................... 503/216; 503/225
[58] Field of Search ............................... 503/216, 225

[56] References Cited

U.S. PATENT DOCUMENTS 3,539,375 11/1970 Baum .................. 117/36.2
4,531,139 7/1985 Seitz .................... 346/201

FOREIGN PATENT DOCUMENTS

| 3401752 | 7/1984 | Fed. Rep. of Germany . |
| 43-4160 | 2/1968 | Japan . |
| 45-14039 | 5/1970 | Japan . |
| 48-27736 | 4/1973 | Japan . |
| 56-146794 | 11/1981 | Japan . |
| 58-199189 | 11/1983 | Japan . |
| 59-114096 | 6/1984 | Japan . |
| 59-167292 | 9/1984 | Japan . |
| 60-78782 | 5/1985 | Japan . |
| 0107389 | 6/1985 | Japan .................. 503/216 |
| 62-121769 | 6/1987 | Japan . |
| 62-164579 | 7/1987 | Japan . |
| 62-169681 | 7/1987 | Japan . |
| 59-93387 | 5/1989 | Japan . |
| 3-38996 | 2/1991 | Japan . |

OTHER PUBLICATIONS

Patent Abstracts of Japan vol. 9, No. 46 (M-360) (1769) Feb. 27 1985.

*Primary Examiner*—Pamela R. Schwartz
*Attorney, Agent, or Firm*—Armstrong, Westerman, Hattori, McLeland & Naughton

[57] ABSTRACT

A thermosensitive recording material capable of recording thereon colored images having high resistances to oily substances, plasticizers, moisture, and heat and an excellent storage persistency over a long time, comprises a thermosensitive colored image-forming layer formed on a sheet substrate and comprising a colorless dye precursor, a color developing agent, and a binder, the color developing agent comprising at least one compound of the formula (I):

$$(R-SO_2NHCNH)_n A \qquad (I)$$
$$\overset{\|}{X}$$

wherein X is an O or S atom, R is an unsubstituted aromatic group or an aromatic group substituted by a lower alkyl or halogen atom; A represents a multivalent group, and n is an integer of 2 or more.

6 Claims, No Drawings

THERMOSENSITIVE RECORDING MATERIAL

BACKGROUND OF THE INVENTION

1. Field of the Invention

The present invention relates to a thermosensitive recording material on which colored images are formed by heating. More particularly, the present invention relates to a thermosensitive recording material capable of forming thereon colored images reluctant to fade and thus exhibiting a high degree of persistency during extended storage thereof.

The thermosensitive recording material of the present invention is capable of recording thereon colored images exhibiting excellent resistance to moisture, heat, oily and fatty substances, and plasticizers, and thus has superior persistency when stored over a long period of time and therefore is useful as colored image-recording sheets, sheets for use in facsimiles, word processors, CRT image printers and cash dispensers, as passenger tickets, commuter passes, labels such as POS labels, cards such as prepaid cards, and as transit passes.

2. Description of the Related Arts

It is known that a conventional thermosensitive recording material comprises a supporting substrate, for example, a paper sheet, synthetic paper sheet, or plastic resin film and a thermosensitive colored image-forming layer formed on a surface of the supporting substrate and comprising an electron-donative dye precursor, for example, a leuco basic dye, an electron-acceptive color-developing agent consisting of an organic acid substance, for example, a phenolic compound, and a binder. When the thermosensitive colored image-forming layer is heated imagewise, colored images are recorded thereon by a reaction of the dye precursor with the color-developing agent.

This type of thermosensitive recording material is disclosed in Japanese Examined Patent Publication Nos. 43-4,160 and 45-14,039 and Japanese Unexamined Patent Publication No. 48-27,736, and is widely employed in practice.

Namely, the thermosensitive recording material is advantageous in that colored images can be easily formed by heating alone, and the recording apparatus can be made compact and small in size, has a relatively low price, and can be easily maintained. Therefore, the thermosensitive recording material is appreciated as a useful information-recording material for recording outputs of printers used with, for example, computers, facsimile machines, automatic ticket-vending machines, scientific measurement recorders, and CRT medical measurement recorders.

Nevertheless, the conventional dye-forming type thermosensitive recording material in which the thermosensitive colored image-forming layer comprises a conventional color-developing agent together with the dye precursor and the binder is disadvantageous in that the resultant colored images fade with the lapse of time, presumably because of a reversible reaction of the dye precursor with the color-developing agent. This fading of the colored images is accelerated by exposure to light, high temperatures, and high humidity and is specifically promoted by contact with an oily or fatty substance or a plasticizer, to such an extent that the faded images cannot be recognized.

Many attempts have been made to retard or inhibit the fading of the colored images formed on a conventional thermosensitive colored image-forming layer containing a substantially colorless dye precursor comprising a lactone ring compound.

For example, Japanese Unexamined Patent Publication Nos. 60-78,782, 59-167,292, 59-114,096 and 59-93,387 disclose a thermosensitive colored image-forming layer containing a phenolic antioxidant.

Japanese Unexamined Patent Publication No. 56-146,794 discloses a protective layer formed from a hydrophobic polymeric compound emulsion on a thermosensitive colored image-forming layer.

Japanese Unexamined Patent Publication No. 58-199,189 discloses formation of both an intermediate layer and a top layer on a thermosensitive colored image-forming layer; the former being formed from a water-soluble polymeric compound solution or a hydrophobic polymeric compound emulsion and the latter being formed from a solvent-soluble hydrophobic polymer on the intermediate layer.

Japanese Unexamined Patent Publication No. 62-164,579 discloses a thermosensitive colored image-forming layer containing an additive consisting of an epoxy compound, which, to some extent, effectively inhibits the fading of the colored images.

Japanese Unexamined Patent Publication No. 62-169,681 discloses metal salts of specific salicylic acid derivatives usable as a color-developing agent.

In the thermosensitive colored image-forming layer containing the phenolic antioxidant, the resultant colored images exhibit a higher resistance to heat and moisture to a certain extent compared to the colored images formed on a conventional colored image-forming layer free from the phenolic antioxidant, but the improvement effect of the phenolic antioxidant is not satisfactorily high. Also, the phenolic antioxidant does not have the capability to enhance the resistance of the colored images to the oily or fatty substances, for example, salad oil, and plasticizers, for example, dioctyl phthalate. The resistance of the colored images to oily or fatty substance or a plasticizer is determined in such a manner that the colored images are brought into contact with an oily or fatty substance, for example, a salad oil or a plasticizer, and left in contact therewith for a predetermined time, and then a retention of the color density of the tested colored images is measured in comparison with an initial color density thereof.

When the protective layer or the intermediate and top layers are formed on the thermosensitive colored image-forming layer, the resultant colored images exhibit a significantly enhanced persistency when the salad oil or the dioctyl phthalate is brought into contact with the colored image-forming surface of the recording material. Nevertheless, when the salad oil or the dioctyl phthalate is brought into contact with an edge face of the recording material, it penetrates the inside of the recording material and causes a complete fading of the colored images. Therefore, the provision of the protecting layer or the intermediate and top layer cannot completely eliminate the undesirable color-fading of the images.

The addition of the epoxy compound to the colored image-forming layer is not totally appreciated, because it takes a long time to stabilize the colored images formed on the colored image-forming layer after a heat-recording operation, and therefore, if an oily or fatty substance, for example, salad oil, or a plasticizer, for example, dioctyl phthalate, is brought into contact with the colored image-forming layer immediately after the heat-recording operation, the resultant colored images fade to a great extent.

The addition of the metal salts of the specific salicylic acid derivative to the colored image-forming layer effectively enhances the resistances of the colored image-forming layer to the oily or fatty substances and to the plasticizers. When the resultant thermosensitive recording sheet is subjected to a colored image-recording procedure and then to a heat resistance test, however, an undesirable color-development occurs on non-image-formed white portions of the recorded sheet. Also, the utilization of the specific salicylic acid derivative metal salts is disadvantageous in that this chemical has a complicated chemical structure and thus is expensive.

In another attempt made to retard or inhibit the fading of the colored images, Japanese Unexamined Patent Publication No. 62-121,769 discloses a utilization of a dimerized fluoran dye.

This dimerized fluoran dye is certainly contributory to enhancing the persistency of the resultant colored images. However, this dimerized fluoran dye undesirably causes the resultant thermosensitive recording sheet to exhibit a lower degree of whiteness and poor heat response, namely heat sensitivity.

In still another attempt made to retard or inhibit the fading of the colored images, Japanese Unexamined Patent Publication No. 3-38,996 discloses a color-forming system not containing a fluoran-type leuco dye. This color-forming system is made from 3-amino-1-imino-4,5,6,7-tetra-chloro-1H-isoindole and 4,4',4''-tri-isocyanato-2,5-dimethoxytriphenylamine which induce an irreversible color-forming reaction.

This irreversible thermosensitive color-forming system produces color images having a high color fastness. However, when the resultant color-forming layer is brought into contact with a plasticizer after applying a thermal recording operation thereto, a non-image formed portion thereof is undesirably colored red and thus the recorded colored images exhibit lowered quality.

SUMMARY OF THE INVENTION

An object of the present invention is to provide a thermosensitive recording material capable of forming colored images thereon having excellent resistance to oily and fatty substances, plasticizers, moisture, and heat, and thus exhibiting superior persistency over a long time.

Another object of the present invention is to provide a thermosensitive recording material useful for thermorecording type tickets of automatic ticket-vending machines, commuter passes, and coupon tickets, which must have high persistency of the colored images recorded thereon, and for label sheets to be used in a POS bar code price-indicating system in which the label sheets are frequently attached to a surface of a polyvinyl chloride film containing a plasticizer and for wrapping fresh food or meat containing an oily or fatty substance; the label sheets of which are unavoidably brought into contact with the plasticizer and/or oily or fatty substance.

A further object of the present invention is to provide a thermosensitive recording material useful as facsimile recording sheets, word processor recording sheets, and CRT image printing sheets, which all must have high persistency of colored images recorded thereon.

The above-mentioned objects can be attained by the thermosensitive recording material of the present invention, which comprises a sheet substrate and a thermosensitive colored image-forming layer formed on a surface of the sheet substrate and comprising a substantially colorless dye precursor, a color developing agent reactive with the dye precursor upon heating to thereby develop a color, and a binder, the color developing agent comprising at least one compound of the formula (I):

wherein X represents a member selected from the group consisting of oxygen and sulfur atoms; R represents a member selected from the group consisting of unsubstituted aromatic hydrocarbon groups and substituted aromatic hydrocarbon groups having at least one substituent selected from the group consisting of lower alkyl groups and halogen atoms; A represents a multivalent group and n represents an integer of 2 or more.

DESCRIPTION OF THE PREFERRED EMBODIMENTS

In the thermosensitive recording material of the present invention, a thermosensitive colored image-forming layer is formed on a surface of a sheet substrate and comprises a substantially colorless dye precursor, a specific color developing agent reactive with the dye precursor upon heating to thereby develop a color, and a binder.

The color developing agent comprises at least one compound of the formula (I) having at least two N-arylsulfonyl(thio) urea group of the formula (II);

wherein X and R are as defined above.

The compound of the formula (I) effectively causes the resultant colored images, even immediately after the formation thereof, to exhibit an excellent resistance to oily and fatty substances and plasticizers, moisture and heat and thus a superior persistency over a long period of time.

The compounds of the formula (I) do not have acidic functional groups, for example, a phenolic hydroxyl group or carboxyl group. Nevertheless, the compounds of the formula (I) exhibit a strong color developing ability for the dye precursor consisting of a basic leuco dye. The reasons for the strong color developing ability have not yet been completely made clear, but it is assumed that the (thio) urea groups in the compounds of the formula (I) are activated by the sulfonyl group located adjacent to the (thio) urea group and exhibit color developing activity.

Also, the reasons for the superior persistency of the colored images developed by the compound of the formula (I) even in various severe circumstances have not yet been completely made clear, but it is presumed that a synergistic effect of the two or more N-arylsulfonyl(thio) urea groups of the formula (II) are highly contributory to stabilizing the resultant colored images.

In the formula (I), the multivalent group represented by A is not limited to specific groups as long as the group has a valency of two or more and is capable of connecting the two or more N-arylsufonyl(thio) urea groups of the formula (II) to each other therethrough. Nevertheless, the multivalent group A is preferably selected from the group consisting of:

(a) divalent carbonyl, thiocarbonyl and sulfonyl groups;

(b) multivalent aliphatic hydrocarbon groups;

(c) multivalent, hetero-atom-containing aliphatic groups derived from aliphatic hydrocarbon compounds having at least one hetero-atom located in a backbone chain per molecule thereof;

(d) multivalent aliphatic groups derived from aliphatic hydrocarbon compounds having at least one member selected from the group consisting of carbonyl, thiocarbonyl, imide, imino, and sulfonyl groups and ester structures, located in a backbone chain per molecule thereof;

(e) multivalent aliphatic aromatic (aroaliphatic) groups derived from aliphatic hydrocarbon compounds having at least one member selected from the group consisting of unsubstituted and substituted aromatic hydrocarbon groups, located in a backbone chain per molecule thereof;

(f) multivalent organic groups derived from aliphatic hydrocarbon compounds having at least one member selected from the group consisting of unsubstituted and substituted hetero-cyclic groups, located in a backbone chain per molecule thereof;

(g) multivalent aromatic groups derived from unsubstituted and substituted aromatic hydrocarbon compounds;

(h) multivalent heterocyclic groups derived from unsubstituted and substituted heterocyclic compounds; and (i) multivalent organic groups derived from organic compounds in which two or more aromatic or heterocyclic groups are bonded to each other through one or more multivalent groups selected from the above-mentioned groups (a) to (d).

The typical multivalent groups standing for A in the formula (I) are as follow.

| Group | Chemical formula |
|---|---|
| (a) | $-\underset{\underset{O}{\|\|}}{C}-, -\underset{\underset{S}{\|\|}}{C}-, -SO_2-$ |
| (b) | $-CH_2-CH_2-, -CH_2-CH-CH_2-,$ <br> $>CHCH_2CH_2CH<$ |
| (c) | $-CH_2CH_2-O-CH_2CH_2-,$ <br> $-CH_2CH_2-N-CH_2CH_2-$ <br> $\phantom{-CH_2CH_2-N}\|$ <br> $\phantom{-CH_2CH_2-N}CH_2CH_2-$ |
| (d) | $-CH_2-\underset{\underset{O}{\|\|}}{C}-CH_2-, -CH_2-\underset{\underset{O}{\|\|}}{C}-OCH_2CH_2-$ |

-continued

| Group | Chemical formula |
|---|---|
| (e) | 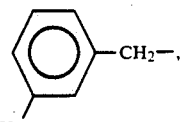 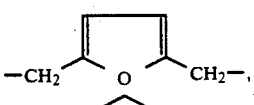 |
| (f) | 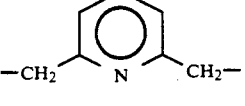 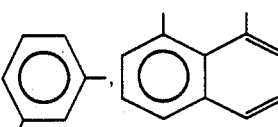 |
| (g) | 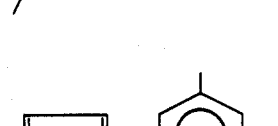 |
| (h) | 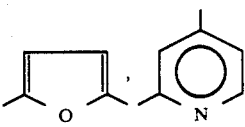 |
| (i) | 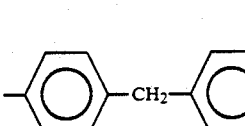 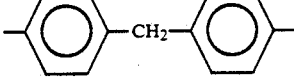 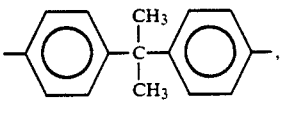 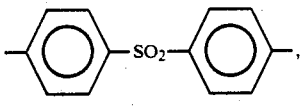 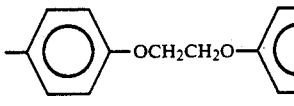 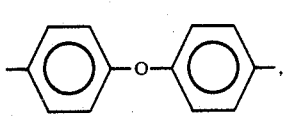 |

| Group | Chemical formula |
| --- | --- |
| | 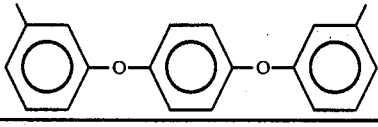 |

In the formula (I), R preferably represents a member selected from the group consisting of p-toluene, o-toluene, 1-naphthalene and p-chloro-benzene groups.

The compounds of the formula (I) include the specific N-arylsulfonyl(thio) urea compounds such as bis(p-toluenesulfonylaminocarbonylamino)ketone, 1,2-bis(p-toluenesulfonylaminocarbonylamino)ethane, 1,1,6,6-tetra(p-toluenesulfonylaminocarbonylamino)heptane, 1,5-bis(p-toluenesulfonylaminocarbonylamino)-3-oxapentane, 1,5-bis(p-toluenesulfonylaminocarbonylamino)-3-thiopentane, 1,3-bis(p-toluenesulfonylaminocarbonylamino)-2-propanone, 1,5-bis(p-toluenesulfonylaminocarbonylamino)-3-(2'-(p-toluenesulfonylaminocarbonylamino)ethyl)-3-azapentane, 1,3-bis(p-toluenesulfonylaminocarbonylaminomethyl)benzene, 1,4-bis(p-toluenesulfonylaminocarbonylamino)benzene, 4,4'-bis(p-toluenesulfonylaminocarbonylamino)diphenylmethane, 4,4'-bis(o-toluenesulfonylaminocarbonylamino)diphenylmethane, 4,4'-bis(benzenesulfonylaminocarbonylamino)diphenylmethane, 4,4'-bis(1-naphthalenesulfonylaminocarbonylamino)diphenylmethane, 4,4'-bis(p-toluenesulfonylaminothiocarbonylamino)diphenyl methane, 2,2-bis(4'-(p-toluenesulfonylaminocarbonylamino)phenyl)propane, 1,2-bis(4'-(p-toluenesulfonylaminocarbonylamino)phenyloxy)ethane, 3,3'-bis(p-toluenesulfonylaminocarbonylamino)diphenylsulfone, 3,3'-bis(p-chlorobenzenesulfonylaminocarbonylamino)diphenylsulfone, 4,4'-bis(p-toluenesulfonylaminocarbonylamino)diphenylether, 2,5-bis(p-toluenesulfonylaminocarbonylaminomethyl)furane, 1,3-bis(p-toluenesulfonylaminocarbonylamino)benzene, 1,4-bis(p-toluenesulfonylaminocarbonylamino)benzene, 1,5-bis(p-toluenesulfonylaminocarbonylamino)naphthalene, 1,8-bis(p-toluenesulfonylaminocarbonylamino)naphthalene, and 1,4-bis(3'-(p-toluenesulfonylaminocarbonylamino)phenyloxy)benzene.

Those compounds can be used alone or as a mixture of two or more thereof.

Nearly all of the N-arylsulfonyl(thio) urea compounds of the formula (I) are novel compounds. The compounds of the formula (I) can be prepared in accordance with the following reactions (1) to (5).

Reaction (1):

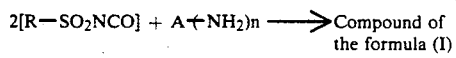

Reaction (2):

Reaction (3):

Reaction (4):

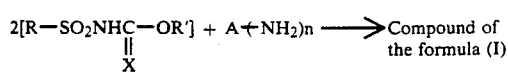

Reaction (5):

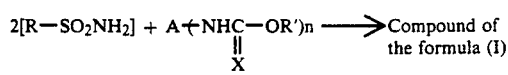

In the above chemical formulae, R, A, X and n are as defined above, and R' represents a member selected from the group consisting of lower alkyl groups having 1 to 8 carbon atoms and a phenyl group.

The reactions are usually carried out in a solvent medium that is not restricted to a specific group of compounds as long as it does not have an activated hydrogen atom and is not reactive with isocyanate compounds.

Nevertheless, to obtain a reaction product not discolored and thus having a high degree of whiteness, the solvent medium preferably consists of at least one non-aromatic compound.

Sometimes, a contact of the compound of the formula (I) with an aromatic compound, for example, xylene and toluene, particularly at a high temperature, causes the compound of the formula (I) to exhibit a lowered degree of whiteness.

The non-aromatic solvent medium for the preparation of the compound of the formula (I) preferably comprises at least one member selected from, for example, halogenated aliphatic compounds, for example, dichloro-methane, chloroform, tetrachloromethane and trichloroethylene; aliphatic nitrile compounds, for example, acetonitrile, and propionitrile; aliphatic ester compounds, for example, ethyl acetate, propyl acetate, and butyl acetate; aliphatic ether compounds, for example, ethyleneglycoldimethylether and dibutylether; and aliphatic ketone compounds, for example, cyclohexanone.

In some of the compounds of the formula (I), the melting point thereof is variable depending on the type of solvent medium and reaction conditions employed in the preparation thereof. The reasons for the variation in the melting point is not clear. Samples of a compound of the formula (I) in question cannot be distinguished from each other by elemental analysis, because they have the same chemical constitution. However, when an X-ray crystal analysis is applied to them, it is found that a sample having an unclear melting point exhibits a reduced sharpness in the peaks of the X-ray crystal analysis chart; the peak sharpness of which is responsive to the crystalline structure of the sample. Therefore, it is presumed that the variation in the melting point depends on the difference in the crystal structure of the samples.

A preferable compound of the formula (I) is 4,4'-bis(p-toluenesulfonylaminocarbonylamino)diphenylmeth ane of the formula (III):

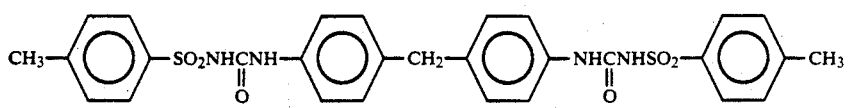

(III)

The compound of the formula (III) can be prepared in accordance with the following reactions (6) and (7):

Reaction (6):

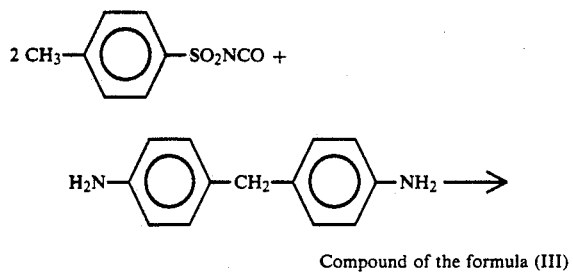

Compound of the formula (III)

Reaction (7):

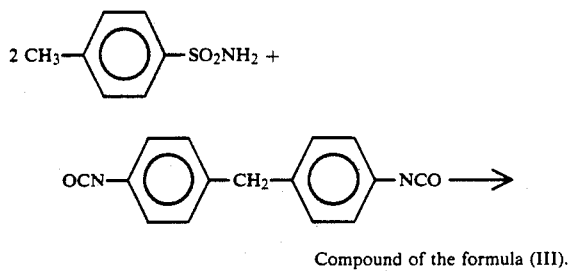

Compound of the formula (III).

The reactions are preferably carried out in a non-aromatic solvent medium as mentioned above.

The dye precursor usable for the present invention comprises at least one member selected from conventional triphenylmethane, fluoran, and diphenylmethane leuco dyes, for example, 3-(4-diethylamino-2-ethoxyphenyl)-3-(1-ethyl-2-methylindole-3-yl)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(2',4'-dimenthylphenylamino) fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino)fluoran, 3-diethylamino-7-(m-trifluoromethylanilino)fluoran, 3-diethylamino-6-methyl-7-chlorofluoran, 3-diethylamino-6-methylfluoran, 3-cyclohexylamino-6-clorofluoran and 3-(N-ethyl-N-hexylamino)-6-methyl-7-(p-chloroanilino) fluoran.

In the thermosensitive colored image-forming layer of the present invention, the color developing agent optionally contains at least one conventional color-developing compound in addition to the N-arylsufonyl(thio)urea compound of the formula (I), unless the color-forming performance of the colored image-forming layer is disturbed thereby.

The conventional color developing compound is preferably selected from the group consisting of 2,2-bis(4-hydroxyphenyl)propane (namely bisphenol A), 1,1-bis(4-hydroxyphenyl)-1-phenylethane, 1,4-bis(1-methyl-1-(4'-hydroxyphenyl)ethyl)benzene, 1,3-bis(1-methyl-1-(4'-hydroxyphenyl)ethyl)benzene, dihydroxydiphenylether (disclosed in JP-A-1-180,382), benzyl p-hydroxy-benzoate (disclosed in JP-A-52-140,483), bisphenol S, 4-hydroxy-4'-isopropyloxy-diphenylsulfone (disclosed in JP-A-60-13,852), 1,1-di-(4-hydroxyphenyl)-cyclohexane, 1,7-di(4-hydroxyphenylthio)-3,5-dioxaheptane (disclosed in JP-A-59-52,694), and 3,3'-diallyl-4,4-dihydroxydiphenylsulfone (disclosed in JP-A-60-208,286).

The above-mentioned conventional color developing compounds can be employed alone or as a mixture of two or more thereof.

The binder usable for the present invention preferably comprises at least one member selected from water-soluble polymeric materials, for example, polyvinyl alcohols of various molecular weights, starch and starch derivatives, cellulose derivatives, for example, methoxy cellulose, carboxymethyl cellulose, methyl cellulose and ethyl cellulose, sodium polyarcylate, polyvinyl pyrrolidone, acrylic acid amide-acrylic acid ester copolymers, acrylic acid amide-acrylic acid ester-methacrylic acid terpolymers, alkali salts of styrene-maleic anhydride copolymers, polyacrylic acid amide, sodium alginate, gelatine and casein, and water-insoluble polymeric materials, for example, polyvinyl acetate resins, polyurethane resins, styrene-butadiene copolymer resins, polyacrylic acid resins, polyacrylic acid ester resins, vinyl chloride-vinyl acetate copolymer resins, polybutyl acrylate, ethylene-vinyl acetate copolymer resins and styrene-butadiene-acrylic compound-terpolymer resins, used in the form of a latex.

In the thermosensitive colored image-forming layer of the present invention, the dye precursor is present in an amount of 5 to 20% of weight, the color developing compound of the formula (I) is present in an amount of 5 to 50% by weight, and the binder is present in an amount of 5 to 20% by weight, based on the total dry weight of the colored image-forming layer.

When the content of the color developing compound of the formula (I) is less than 5% by weight, the resultant thermosensitive colored image-forming layer exhibits an unsatisfactory color-forming performance, and when the content of the color developing compound of the formula (I) is more than 50% by weight, the resultant color-developing performance is saturated, and thus the resultant recording material is sometimes economically disadvantageous.

When the conventional color developing compound is employed, its content in the color image-forming layer is preferably 5 to 40% by weight.

The thermosensitive colored image-forming layer of the present invention optionally further comprises a heat-fusible organic substance, usually referred to as a sensitizer, inorganic and organic pigments, antioxidants, for example, hindered phenol compounds, ultraviolet ray-absorbers, and waxes.

The sensitizer comprises at least one organic compound having a melting point of from 50° C. to 150° C., for example, phenyl 1-hydroxy-2-naphthoate (JP-A-57-191,089), p-benzyl-biphenyl (JP-A-60-82,382), benzyl naphthyl ether (JP-A-58-87,094), dibenzyl terephthalete (JP-A-58-98,285), benzyl p-benzyloxybenxoate (JP-A-

57-201,691), diphenyl carbonate, ditolyl carbonate (JP-A-58-136,489), m-terphenyl (JP-A-57-89,994), 1,2-bis(m-tolyloxy)ethane (JP-A-60-56,588), 1,5-bis(p-methoxyphenoxy)-3-oxapentane (JP-A-62-181,183), oxalic acid diesters (JP-A-64-1,583) and 1,4-bis(p-tolyloxy)benzene (JP-A-2-153,783).

The antioxidant and ultraviolet ray-absorbers are preferably selected from those disclosed in JP-A-57-151,394, JP-A-58-160,191, JP-A-58-69,096, JP-A-59-2,884, JP-A-59-95,190, JP-A-60-22,288, JP-A-60-255,485, JP-A-61-44,686, JP-A-62-169,683, JP-A-63-17,081 and JP-A-1-249,385, for example, 1,1,3-tris(3'-cyclohexyl-4'-hydroxyphenyl) butane; 1,1,3-tris(2-methyl-4-hydroxy-5-tert-butylphenyl)butane, 4,4'-thiobis(3-methyl-6-tert-bytylphenol), 1,3,5-trimethyl-2,4,6-tris(3,5-di-tert-butyl-4-hydroxybenzyl)benzene, 2,2'-dihydroxy-4, 4'-dimethoxybenzophenone, p-octylphenyl salycilate, 2-(2'-hydroxy-5'-methylphenyl)benzotriazole, ethyl-2-cyano-3,3'-diphenyl acrylate, and tetra(2,2,6,6-tetramethyl-4-piperidyl)-1,2,3,4-butane -tetracarbonate.

The inorganic and organic pigments usable for the present invention are preferably selected from inorganic fine particles of, for example, calcium carbonate, silica, zinc oxide, titanium dioxide, aluminum hydroxide, zinc hydroxide, barium sulfate, clay, anhydrous clay, talc, and surface-treated calcium carbonate and silica and organic fine particles of, for example, urea-formaldehyde resins, styrene-methacrylate copolymer resins and polystyrene resins.

The waxes usable for the present invention preferably comprises at least one member selected from, for example, paraffin waxes, carnauba wax, microcrystalline waxes, polyethylene waxes, amide type waxes, bisimide type waxes, higher fatty acid amide waxes, for example, stearic acid amide, ethylene-bis-stearoamide wax, higher fatty acid esters and metal salts, for example, zinc stearate, aluminum sterrate, calcium stearate, and zinc oleate.

In the colored image forming layer of the present invention, the sensitizing agent is preferably contained in an amount of 5 to 40% by weight, the wax and organic or inorganic pigment are optionally contained in amounts of 2 to 20% by weight and 5 to 50% by weight, respectively, and the antioxidant and ultraviolet ray-absorber are optionally contained in an amount of 1 to 10%, based on the total dry weight of the colored image-forming layer.

The sheet substrate usable for the present invention is not limited to a specific group of materials, and usually the sheet substrate comprises a member selected from fine paper sheets, coated paper sheets having a clay or latex-coated layer, cast-coated paper sheets, paper boards, plastic resin films, synthetic paper sheets comprising a plastic resin such as a polyolefin resin and a multi-layer structure, and laminated composite sheets. Preferably, the sheet substrate has a basis weight of 40 to 170 g/m$^2$.

The colored image-forming layer can be formed on a surface of sheet substrate, by applying a coating liquid containing the above-mentioned components, and by drying and solidifying the coating liquid layer on the sheet substrate.

The colored image-forming layer is preferably present in a dry weight of from 1 to 15 g/m$^2$, more preferably 2 to 10 g/m$^2$.

In the present thermosensitive recording material, a protective layer and/or a layer for printing may be formed on the colored image-forming layer.

In the thermosensitive recording material of the present invention, the novel color developing compounds of the formula (I) having two or more N-arylsulfonyl(thio) urea groups per molecule thereof exhibit a color-developing activity comparative to or higher than that of bisphenol A which is a typical conventional color developing compound.

Also, the color developing compound of the formula (I) effectively causes the resultant colored images to exhibit an excellent resistance to oily and fatty substances and a plasticizer even immediately after the color development, and thus have a superior storage persistency.

EXAMPLES

The present invention will be further explained by the following specific examples, which are merely representative and do not in any way restrict the scope of the present invention.

SYNTHESIS EXAMPLE 1

Preparation (I) of
4,4'-bis(p-toluenesulfonylaminocarbonylamino)diphenylmethane

A three-necked flask equipped with a dropping funnel and a thermometer was charged with 9.9 g of 4,4'-diaminodiphenylmethane, and this compound was dissolved in 200 ml of acetonitrile. While the resultant reaction solution was vigorously stirred with a magnetic stirrer, 21.7 g of toluenesulfonylisocyanate were added from the dropping funnel to the reaction solution. Upon the dropwise addition is started, an exothermic reaction occurred and a slightly yellow colored solid was precipitated. The resultant reaction mixture was further stirred for one hour, and then filtered. White crystals were obtained in an amount of 29.2 g.

NMR measurement, mass spectrometric analysis, and IR measurement identified the resultant crystals as the aimed compound.

The crystals had a melting point of from 160° C. to 164° C., which sometimes varied.

The white crystals were subjected to an elemental analysis.

The results of the analysis are shown in Table 1.

TABLE 1

| Item | Carbon (%) | Hydrogen (%) | Oxygen (%) | Nitrogen (%) | Sulfur (%) |
|---|---|---|---|---|---|
| Calculated value | 58.8 | 4.8 | 16.2 | 9.5 | 10.8 |
| Measured value | 58.8 | 4.9 | 16.0 | 9.5 | 11.0 |

NMR measurement (in deuterized acetone, ppm).
$\delta$=2.40 (s, 6H), 3.83 (s, 2H), 7.11 (d, 4H).
7.35 (t, 8H), 7.92 (d, 4H).

Also, peaks, which are presumably derived from protons of —N—H group, were appeared at $\delta$=about 8.3 and at $\delta$=9.6.

IR measurement (KBr tablet method) characteristic absorptions 1670 cm$^{-1}$ (derived from carbonyl group in urea groups).

1345 cm$^{-1}$ and 1160 cm$^{-1}$ (derived from sulfonyl groups).

SYNTHESIS EXAMPLE 2

Preparation (II) of 4,4'-bis(p-toluenesulfonylaminocarbonylamino)diphenyl-methane The same synthesis procedures as in Synthesis Example 1 were carried out except that acetonitrile was replaced by dichloromethane.

Slightly yellow-colored 4,4'-bis(p-toluenesulfonylaminocarbonylamino)diphenylmethane was obtained.

The identification test results were the same as in Synthesis Example 1 except that the melting point of the product could not be clearly determined in the range of upto 220° C.

SYNTHESIS EXAMPLE 3

Preparation (III) of 4,4'-bis(p-toluenesulfonylaminocarbonylamino)diphenylmethane The same procedures as in Synthesis Example 1 were carried out except that acetonitrile was replaced by ethyl acetate.

White 4,4'-bis(p-toluenesulfonylaminocarbonylamino)diphenylmethane was obtained.

The identification test results were the same as in Synthesis Example 1.

SYNTHESIS EXAMPLE 4

Preparation (IV) of 4,4'-bis(p-toluenesulfonylaminocarbonylamino)diphenylmethane Kjeldahl flask was filled with dry nitrogen gas and charged with 10.0 g of 4,4'-diphenylmethanediisocyanate and 14.4 g of p-toluenesulfoneamide. The mixture of the above-mentioned compounds was subjected to a reaction by heating at a temperature of 140° C. in the nitrogen gas atmosphere. About one hour after the start of the reaction, the reaction mixture was solidified. After cooling, the solid product was extracted in an 1N aqueous sodium hydroxide solution. When the resultant extract solution was acidified, a white solid was precipitated.

By HPLC analysis, it was confirmed that the resultant white solid product was the same compound as in Synthesis Example 1.

SYNTHESIS EXAMPLE 5

Preparation of 1,8-bis(p-toluenesulfonylaminocarbonylamino)naphthalene

The same procedures as in Synthesis Example 1 were carried out except that 9.9 g of 4,4'-diaminodiphenylmethane were replaced by 16.0 g of 1,8-diaminonaphthalene, and toluenesulfonylisocyanate was employed in an amount of 41.0 g.

A white crystals were obtained in an amount of 47.6 g.

This compound exhibited a thermal decomposition temperature of 145° C.

NMR measurement, mass spectrometric analysis and IR measurement confirmed that the resultant product was the aimed compound.

NMR measurement (in denterized DMSO).

$\delta = 2.39$ (s, 6H), 7.05-7.9 (m, 14H)).

Additionally, the peaks, which are presumably derived from N-H group, appeared at $\delta =$ about 8.9 and at $\delta =$ about 10.5.

IR measurement (KBr tablet method).

Characteristic absorptions were confirmed as follows.

1665 cm$^{-1}$ derived from carbonyl groups in urea groups.

1355 cm and 1160 cm$^{-1}$ derived from a sulfonyl groups.

SYNTHESIS EXAMPLE 6

Preparation of 3,3'-bis(p-toluenesulfonylaminocarbonylamino)diphenylsulfone

The same procedures as in Synthesis Example 1 were carried out except that 9.9 g of 4,4'-diaminodiphenylmethane were replaced by 10.0 g of 3,3'-diaminodiphenylsulfone, this 3,3'-diaminodiphenylsulfone was dispersed in 300 ml of dichloromethane replaced for acetonitrile, and then 18.6 g of toluenesulfonylisocyanate was added to the dispersion.

White crystals were obtained in an amount of 27.4 g. The white crystals had a melting point of 220° C. or higher.

NMR measurement, mass spectrometric analysis and IR measurement confirmed that the resultant product was the aimed compound.

NMR measurement (in denterized DMSO).

$\delta = 2.40$ (s, 6H), 7.4-8.1 (m, 16H).

Additionally, the peaks, which are presumably derived from N-H group, appeared at $\delta =$ about 9.3 and at $\delta =$ about 11.0.

IR measurement (KBr tablet method).

Characteristic absorptions were confirmed as follows.

1700 cm$^{-1}$ which is derived from carbonyl groups in urea groups.

1342 cm$^{-1}$ and 1155 cm$^{-1}$ which are derived from a sulfonyl groups.

SYNTHESIS EXAMPLE 7

Preparation of 1,3-bis(p-toluenesulfonylaminocarbonylaminomethyl)-benzene

The same procedures as in Synthesis Example 1 were carried out except that 9.9 g of 4,4'-diaminodiphenylmethane were replaced by 6.8 g of m-xylilenediamine and toluenesulfonylisocyanate was employed in an amount of 21.7 g. White crystals were obtained in an amount of 25.8 g. The crystals had a melting point of 198° C.

NMR measurement, mass spectrometric analysis and IR measurements confirmed that the resultant product was the aimed compound.

SYNTHESIS EXAMPLE 8

Preparation of 4,4'-bis-(p-toluenesulfonylaminocarbonylamino)diphenylether

A three-necked flask equipped with a dropping funnel and a thermometer was charged with 8.6 g of 4,4'-diaminodiphenylether and this compound was dispersed in 300 ml of toluene.

While the resultant suspension was vigorously stirred with a magnetic stirrer, 20.5 g of toluenesulfonylisocyanate were added from the dropping funnel to the reaction suspension.

Simultaneously with the dropwise addition, an exothermic reaction occurred and the viscosity of the reaction suspension was raised. After stirring at room temperature for 30 minutes, the reaction suspension was heated at a temperature of 90° C. and maintained at this temperature for 30 minutes. After cooling, the resultant reaction mixture was filtered. White crystals were obtained in an amount of 24.7 g. The crystals had a melting point of 220° C. or higher.

NMR measurement, mass spectrometric analysis and IR measurement identified that the resultant product was the aimed compound.

NMR measurement (in deuterized DMSO).

$\delta = 2.40$ (s, 6H), 6.88 (s, 4H), 7.31 (d, 4H), 7.73 (d, 4H), 7.86 (d, 4H).

Additionally, the peaks, which are presumably derived from N-H group, appeared at $\delta =$ about 8.8 and at $\delta =$ about 10.6.

IR measurement (KBr tablet method).

Characteristic absorptions were as follows.

1650 $cm^{-1}$ and 1668 $cm^{-1}$ (derived from carbonyl groups in urea groups).

1342 $cm^{-1}$ and 1160 $cm^{-1}$ (derived from sulfonyl groups).

EXAMPLE 1

A thermosensitive recording paper sheet was prepared by the following procedures.

(1) Preparation of an aqueous dye precursor dispersion A in the following composition

| Component | Part by weight |
| --- | --- |
| 3-(N-isopentyl-N-ethylamino)-6-methyl-7-anilinofluoran | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(2) Preparation of an aqueous color-developing agent dispersion B in the following composition

| Component | Part by weight |
| --- | --- |
| 4,4'-bis(p-toluenesulfonylaminocarbonylamino)diphenylmethane (Synthesis Example 1) | 10 |
| Di-p-methylbenzyl oxalate | 10 |
| 10% aqueous solution of polyvinyl alcohol | 10 |
| Water | 70 |

The composition was dispersed in a sand grinder to an extent such that the resultant dispersed solid particles had an average size of 1 μm or less.

(3) Preparation of a pigment-coated paper sheet

A coating liquid was prepared by mixing an aqueous dispersion, prepared by dispersing 85 parts by weight of anhydrous clay available under the trademark of Ansilex, from Engelhard Corporation, in 320 parts by weight of water, with 40 parts by weight of an aqueous emulsion of a styrene-butadiene copolymer in a solid concentration of 50% by weight and 50 parts by weight of a 10% aqueous oxidized starch solution.

The coating liquid was coated on a surface of a fine paper sheet having a basis weight of 48 g/$m^2$, to form a coating layer having a dry weight of 7.0 g.$m^2$, whereby a coated paper sheet was obtained.

(4) Formation of thermosensitive colored image-forming layer

A coating liquid was prepared by mixing 50 parts by weight of the aqueous dye precursor dispersion A and 200 parts by weight of the aqueous color-developing agent dispersion B with 30 parts by weight of a calcium carbonate pigment, 20 parts by weight of a 25% aqueous zinc stearate dispersion, 15 parts by weight of 30% aqueous paraffin dispersion, and 100 parts by weight of a 10% aqueous polyvinyl alcohol solution, by agitating the mixture.

A surface of the pigment coated paper sheet was coated with the resultant coating liquid and dried. A thermosensitive colored image-forming layer was formed with a weight of 5.0 g/$m^2$, to provide a thermosensitive recording paper sheet.

(5) Calendering treatment

The recording sheet was treated by a super calender, and the calendered surface of the recording sheet had a Bekk smoothness of 600 to 1000 seconds.

(6) Color-forming test and plasticizer or oil resistance test

A specimen of the resultant thermosensitive recording sheet was subjected to a colored image-developing test with an applied energy of 0.49 mj/dot by using a dynamic color-developing tester provided by modifying a thermosensitive facsimile printer. The resultant black colored images were subjected to a measurement of a color density by a Macbeth Reflection Color Density Tester RD-914 (trademarks). The measured color density is referred to an initial color density of the colored images.

Specimens of the color image-formed recording sheet were subjected to a plasticizer resistance test in the following manner.

Within 30 minutes from the completion of the color developing operation, a colored image-formed surface of a specimen was coated with a salad oil or dioctyl terephthalate, which is a typical plasticizer, and left to stand at room temperature for 3 hours. Then, the salad oil or plasticizer was wiped away form the specimen and the color density of the colored images retained on the specimen was measured by a Macbeth Reflection Color Density Tester. The measured color density is referred to a color density of oil or plasticizer-treated colored images.

The retention in color density of the colored images was calculated in accordance with the following equation:

$$CIR (\%) = \frac{D}{D_0} \times 100$$

wherein CIR represents the retention (%) in color density of the colored images; $D_O$ represents the initial color density of the colored images and D represents the color density of oil or plasticizer-treated colored images.

The test results are shown in Table 2.

EXAMPLE 2

A thermosensitive recording sheet was produced and tested by the same procedures as in Example 1 except that, in the preparation of the dispersion B, the 4,4'-bis(p-toluenesulfonylaminocarbonylamino)diphenylmethane was replaced by 3,3'-bis(p-toluenesulfonylaminocarbonylamino)diphenylsulfone (Synthesis Example 6).

The test results are shown in Table 2.

EXAMPLE 3

A thermosensitive recording sheet was produced and tested by the same procedures as in Example 1 except that, in the preparation of the dispersion B, the 4,4'-bis(p-toluenesulfonylaminocarbonylamino)diphenylmethane was replaced by 4,4'-bis(p-toluenesulfonylaminocarbonylamino)diphenylether, and the di-p-methylbenzyl oxalate was replaced by dibenzyl oxalate.

The test results are shown in Table 2.

EXAMPLE 4

A thermosensitive recording sheet was produced and tested by the same procedures as in Example 1 except that in the formation of the thermosensitive colored image-forming layer, a coating liquid was prepared by mixing 40 parts by weight of the dispersion A and 120 parts by weight of the dispersion B with 40 parts by weight of a calcium carbonate pigment, 20 parts by weight of a 25% aqueous zinc stearate dispersion, 15 parts by weight of a 30% aqueous paraffin dispersion, 120 parts by weight of a 10% aqueous polyvinyl alcohol solution and 3 parts by weight of a wetting agent (available under the trademark of Dupro U99 from SAN-NOPCO K. K.), while stirring the mixture, and the coating liquid was coated on a surface of a synthetic paper sheet (available under the trademark of Yupo FPG-110, from OJI Yuka Goseishi KK), and dried to form a thermosensitive colored image-forming layer having a weight of 8.5 g/m$^2$.

The test results are shown in Table 2.

EXAMPLE 5

A thermosensitive recording sheet was produced and tested by the same procedures as in Example 1, except that in the preparation of the dye precursor dispersion A, the 3-(N-isopentyl-N-ethylamino)-6-methyl-7-anilinofluoran was replaced by 3-(N,N-dibutylamino)-6-methyl-7-anilino-fluoran.

The test results are shown in Table 1.

COMPARATIVE EXAMPLE 1

A thermosensitive recording sheet was produced and tested by the same procedures as in Example 1 except that the 4,4'-bis(p-toluenesulfonylaminocarbonylamino)diphenylmethane was replaced by 2,2'-bis(4-hydroxyphenylpropane) (namely bisphenol A).

The test results are shown in Table 2.

TABLE 2

| Example No. | Initial color density of colored images (D$_0$) | Retention in color density of colored images (%) Salad oil test | Retention in color density of colored images (%) Dioctyl phthalate test |
|---|---|---|---|
| Example 1 | 1.44 | 98 | 89 |
| 2 | 1.35 | 96 | 89 |
| 3 | 1.34 | 96 | 84 |
| 4 | 1.41 | 98 | 88 |
| 5 | 1.33 | 94 | 81 |
| Comparative Example 1 | 1.44 | 20 | 12 |

Table 2 clearly shows that the colored images formed in the thermosensitive colored image-forming layer of Examples 1 to 5 containing the color developing compound of the formula (I) exhibited excellent resistance to the oily and fatty substance and to the plasticizer even immediately after the formation of the images, compared with those of Comparative Example 1 in which a typical conventional color developing agent consisting of bisphenol A was used.

We claim:

1. A thermosensitive recording material comprising:
    a sheet substrate and
    a thermosensitive colored image-forming layer formed on a surface of the sheet substrate and comprising a substantially colorless dye precursor, a color developing agent reactive with the dye precursor upon heating to thereby develop a color, and a binder,
    said color developing agent comprising at least one compound of the formula (I):

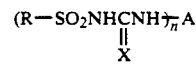

$$(R-SO_2NHCNH)_{\overline{n}}A \qquad (I)$$
$$\phantom{(R-SO_2NHCNH)}\|\phantom{)_{\overline{n}}A}$$
$$\phantom{(R-SO_2NHCNH)}X$$

wherein X represents a member selected from the group consisting of oxygen and sulfur atoms, R represents a member selected from the group consisting of unsubstituted aromatic hydrocarbon groups and substituted aromatic hydrocarbon groups having at least one substituent selected from the group consisting of lower alkyl groups and halogen atoms; A represents a multivalent group, and n represents an integer of 2 or more.

2. The thermosensitive recording material as claimed in claim 1, wherein the multivalent group represented by A in the formula (I) is selected from the group consisting of:
    (a) divalent carbonyl, thiocarbonyl and sulfonyl group;
    (b) multivalent aliphatic hydrocarbon groups;
    (c) multivalent, hetero-atom-containing aliphatic groups derived from aliphatic hydrocarbon compounds having at least one hetero-atom located in a backbone chain per molecule thereof;
    (d) multivalent aliphatic groups derived from aliphatic hydrocarbon compounds having at least one member selected from the group consisting of carbonyl, thiocarbonyl, imide, imino, and sulfonyl groups and ester structures, located in a backbone chain per molecule thereof;
    (e) multivalent aliphatic aromatic groups derived from aliphatic hydrocarbon compounds having at least one member selected from the group consisting of unsubstituted and substituted aromatic hydrocarbon groups, located in a backbone chain per molecule thereof;

(f) multivalent organic groups derived from aliphatic hydrocarbon compounds having at least one member selected from the group consisting of unsubstituted and substituted hetero-cyclic groups, located in a backbone chain per molecule thereof;

(g) multivalent aromatic groups derived from unsubstituted and substituted aromatic hydrocarbon compounds;

(h) multivalent heterocyclic groups derived from unsubstituted and substituted heterocyclic compounds; and (i) multivalent organic groups derived from organic compounds in which two or more aromatic or heterocyclic groups are bonded to each other through one or more multivalent groups selected from the above-mentioned groups (a) to (d).

3. The thermosensitive recording material as claimed in claim 1, wherein the multivalent group represented by A in the formula (I) is selected from the group consisting of:

(a) $-\underset{\underset{O}{\|}}{C}-$, $-\underset{\underset{S}{\|}}{C}-$, $-SO_2-$, (b) $-CH_2-CH_2-$, $-CH_2-CH-CH_2-$, $>CHCH_2CH_2CH<$ (c) $-CH_2CH_2-O-CH_2CH_2-$,
$-CH_2CH_2-\underset{\underset{CH_2CH_2-}{|}}{N}-CH_2CH_2-$ (d) $-CH_2-\underset{\underset{O}{\|}}{C}-CH_2-$, $-CH_2-\underset{\underset{O}{\|}}{C}-OCH_2CH_2-$ (e) 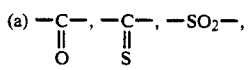

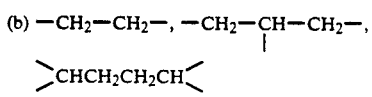

(f) 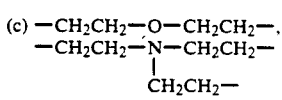

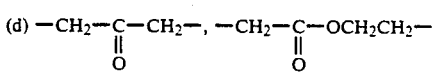

(g) 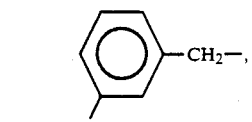

(h) 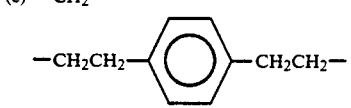

(i) 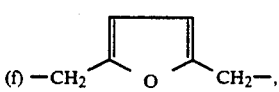

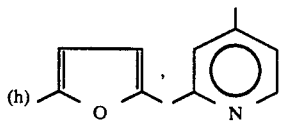

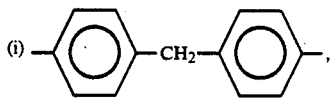

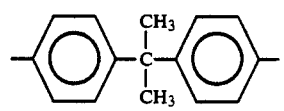

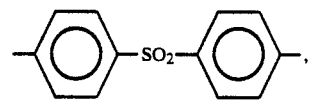

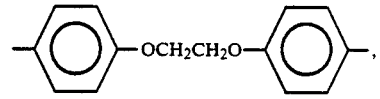

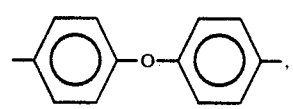

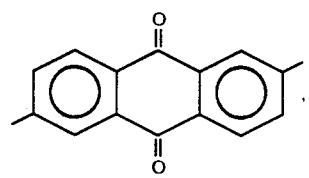

and

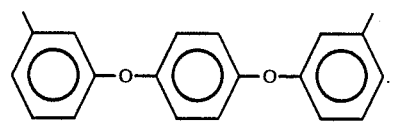

4. The thermosensitive recording material as claimed in claim 1, wherein the compound of the formula (I) is selected from the group consisting of: bis(p-toluenesulfonylaminocarbonylamino)ketone, 1,2-bis(p-toluenesulfonylaminocarbonylamino)ethane, 1,1,6,6-tetra(p-toluenesulfonylaminocarbonylamino)heptane, 1,5-bis(p-toluenesulfonylaminocarbonylamino)-3-oxapentane, 1,5-bis(p-toluenesulfonylaminocarbonylamino)-3-thiopentane, 1,3-bis(p-toluenesulfonylaminocarbonylamino)-2-propanone, 1,5-bis(p-toluenesulfonylaminocarbonylamino)-3-(2'-(p-toluenesulfonylaminocarbonylamino)ethyl)-3-azapentane, 1,3-bis(p-toluenesulfonylaminocarbonylaminomethyl)benzene, 1,4-bis(p-toluenesulfonylaminocarbonylamino)benzene, 4,4'-bis(p-toluenesulfonylaminocarbonylamino)diphenylmethane, 4,4'-bis(o-toluenesulfonylaminocarbonylamino)diphenylmethane, 4,4'-bis(benzenesulfonylaminocarbonylamino)diphenylmethane, 4,4'-bis(1-naphthalenesulfonylaminocarbonylamino)diphenylmethane, 4,4'-bis(p-toluenesulfonylaminothiocarbonylamino)diphenylmethane, 2,2-bis(4'-(p-toluenesulfonylaminocabonyl-amino)phenyl)propane, 1,2-bis(4'-(p-toluenesulfonyl-aminocarbonylamino)phenyloxy)ethane, 3,3'-bis(p-toluenesulfonylaminocarbonylamino)diphenyl-sulfone, 3,3'-bis(p-chlorobenzenesulfonylaminocarbonylamino)diphenyl-sulfone, 4,4'-bis(p-toluenesulfonylaminocarbonylamino)diphenylether, 2,5-bis(p-toluenesulfonylaminocarbonylaminomethyl)furane, 1,3-bis(p-toluenesulfonylaminocarbonylamino)benzene, 1,4-bis(p-toluenesulfonylaminocarbonylamino)benzene, 1,5-bis(p-toluenesulfonylaminocarbonylamino)naphthalene, 1,8-bis(p-toluenesulfonylaminocarbonylamino)naphthalene, and 1,4-bis(3'-(p-toluenesulfonylaminocarbonylamino)phenyloxy)benzene.

5. The thermosensitive recording material as claimed in claim 1, wherein the compound of the formula (I) is present in an amount of 5 to 50% based on the total dry weight of the thermosensitive colored image-forming layer.

6. The thermosensitive recording material as claimed in claim 1, wherein the compound of the formula (I) is 4,4'-bis(p-toluenesulfonylaminocarbonylamino)diphenylmethane of the formula:

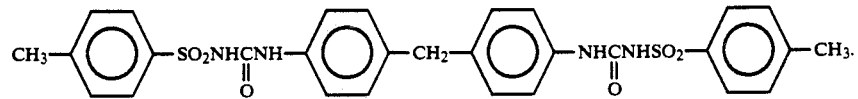

* * * * *